US00PP15291P2

(12) United States Plant Patent
Zaiger et al.

(10) Patent No.: US PP15,291 P2
(45) Date of Patent: Nov. 2, 2004

(54) NECTARINE TREE NAMED 'HONEY DIVA'

(50) Latin Name: ***Prunus persica* var. *nucipersica***
Varietal Denomination: Honey Diva

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/746,712

(22) Filed: Dec. 29, 2003

(51) Int. Cl.[7] ..... A01H 5/00
(52) U.S. Cl. ..... Plt./190
(58) Field of Search ..... Plt./190

*Primary Examiner*—Anne Marie Grunberg

(57) ABSTRACT

A new and distinct variety of nectarine tree (*Prunus persica* var. *nucipersica*). The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Regular and heavy production of fruit.
2. Fruit with very good eating quality, mild, sweet, low-acid flavor.
3. Late fruit maturity with an attractive red skin color.
4. Fruit with good storage and shipping quality.
5. Vigorous and upright growth of tree.
6. Fruit holding firm on the tree 10 to 12 days after maturity, shipping ripe.

1 Drawing Sheet

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of nectarine tree was originated and asexually reproduced by us in our experimental orchard located near Modesto, Stanislaus County, Calif.

2. Prior Varieties

Among the existing varieties of nectarines and peaches, which are known to us, and mentioned herein, 'May Glo' Nectarine (U.S. Plant Pat. No. 5,245), 'O'Henry' Peach (U.S. Plant Pat. No. 2,964), 'June Lady' Peach (U.S. Plant Pat. No. 3,022), 'May Crest' Peach (U.S. Plant Pat. No. 4,064) and 'Honey Royale' Nectarine (U.S. Plant Pat. No. 12,008).

STATEMENT REGARDING FEDERALLY SPONSORED RESEARCH AND DEVELOPMENT

Not applicable.

ORIGIN OF THE VARIETY

The new and distinct variety of nectarine tree (*Prunus persica* var. *nucipersica*) was developed by us in our experimental orchard from seed of an open pollinated nectarine seedling which originated from a cross between proprietary parents with field identification numbers 3RB305 and 10RB220. The maternal parent (3RB305) originated from crosses between the following varieties and proprietary selections; 'O'Henry' Peach (U.S. Plant Pat. No. 2,964), 'June Lady' Peach (U.S. Plant Pat. No. 3,022), Dwarf #514 (proprietary nectarine) and 6W120 (proprietary nectarine). The paternal parent (10RB220) originated from crosses between the following selections and varieties; 'May Glo' Nectarine (U.S. Plant Pat. No. 5,245), 'May Crest' Peach (U.S. Plant Pat. No. 4,064), '#14' (proprietary nectarine) and '20E246' (proprietary nectarine). We planted and grew a large number of these open pollinated seedlings on their own root system, under close and careful observation during which time we recognized the desirable fruit characteristics of the present nectarine variety and selected it in 1996 for asexual propagation and commercialization.

ASEXUAL REPRODUCTION OF THE VARIETY

Asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new nectarine tree (*Prunus persica* var. *nucipersica*) is of large size, vigorous, upright growth and a productive and regular bearer of large size, yellow flesh, clingstone fruit, with very good flavor and eating quality. The fruit is further characterized by having firm flesh with good handling and shipping quality, the flesh being moderately juicy with a mild, sweet, low-acid flavor and having a high degree of attractive red skin color. In comparison to the 'May Glo' Nectarine (U.S. Plant Pat. No. 5,245), the tree requires approximately 400 hours more winter chilling, the flesh of the new variety is low-acid instead of acidic and the fruit is larger in size. In comparison to the 'Honey Royale' Nectarine (U.S. Plant Pat. No. 12,008), the new variety is very similar in flavor and eating quality and is approximately 1 month later in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place.

The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 5 year old specimens grown near Modesto, Calif., with color in accordance with Munsell Book of Color.

Tree:

*Size.*—Large. Pruned to 3 or 3.5 meters in height at maturity for economical harvesting of fruit.

*Vigor.*—Vigorous. Growth of 1.5 to 2 meters the first growing season. Varies with type of soil, fertility and cultural practices.

*Form.*—Upright. Usually pruned to vase shape.

*Branching habit.*—Upright. Crotch angle approximately 35°. Heavy fruit production increases crotch angle.

*Productivity.*—Productive. Usually sets 1½ or more times the amount of fruit desired, thinning and spacing are necessary to develop desired market size fruit.

*Bearer.*—Regular. Has had heavy production 3 consecutive years.

*Fertility.*—Self-fertile.

*Density.*—Medium dense. Usually pruned to vase shape by removing center branches and foliage to increase sunlight and air movement throughout tree.

*Hardiness.*—Hardy in all stone fruit growing areas in California. Trees growing in USDA Hardiness Zone 9. Winter chilling requirement of approximately 700 hours at or below 45° F.

Trunk:

*Size.*—Medium. Average circumference 43.2 cm at 48.6 cm above ground.

*Stocky.*—Medium stocky.

*Texture.*—Medium rough, becomes rougher with age.

*Color.*—Varies from 10YR 5/2 to 10YR 5/4, color darkens with age.

Branches:

*Size.*—Medium. Average circumference 21.6 cm at 1.2 meters above ground.

*Surface texture.*—Smooth to medium rough, varies with age of growth.

*Lenticels.*—Average number of 39 in a 25.8 square cm section. Average length 2.0 mm. Average width 1.3 mm. Color varies from 5YR 4/4 to 5YR 4/6, varies with age of growth.

*Color.*—New growth varies from 2.5YR 7/6 to 2.5YR 4/8 where exposed to sun and 2.5GY 5/6 to 2.5GY 6/6 in the shade. Old growth varies from 5YR 4/4 to 5YR 3/6, varies with age of growth.

Leaves:

*Size.*—Large. Average length 148.1 mm. Average width 41.5 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins. Lower surface relatively smooth with small ridges created by midrib and pinnate venation. Both surfaces glabrous.

*Petiole.*—Medium size. Average length 10.1 mm. Average width 1.4 mm. Glabrous. Color varies from 5GY 6/6 to 2.5GY 6/6.

*Glands.*—Reniform. Small to medium size. Average length 1.0 mm. Average width 0.5 mm. Number varies from 1 to 4, average number 2. Located on the base of the leaf blade and the upper portion of the petiole. Color varies from 2.5YR 5/8 to 5YR 7/8 on lower, outer surface.

*Color.*—Upper surface varies from 2.5GY 4/4 to 5GY 4/6. Lower surface varies from 2.5GY 5/6 to 5GY 6/6. Midvein color varies from 2.5GY 6/6 to 10Y 8/4.

Flower buds:

*Size.*—Large. Average length 16.8 mm. Average diameter 11.3 mm.

*Hardiness.*—Hardy in all stone fruit growing areas of California.

*Form.*—Plump, conical, becoming elongated before opening.

*Pedicel.*—Average length 3.7 mm. Average width 1.7 mm. Color 2.5GY 7/12.

*Color.*— 5RP 7/6.

Flowers:

*Size.*—Large, showy. Average height 21.6 mm. Average diameter 32.9 mm.

*Petals.*—Number 5, alternately arranged to sepals. Shape — orbicular. Average length 15.9 mm. Average width 15.0 mm. Margin varies from entire to sinuate. Color 2.5RP 8/6.

*Sepals.*—Number 5, alternately arranged to petals. Shape — obtuse, apex rounded. Pubescence — inner surface glabrous, outer surface pubescent. Average length 5.0 mm. Average width 4.1 mm. Color — inner surface 2.5GY 6/8. Outer surface 10RP 3/4.

*Stamens.*—Average number per flower 39. Average filament length 13.7 mm. Filament color varies from N 9.5/ to 2.5RP 4/12. Anther color 3.75R 4/14.

*Pollen.*—Present, self-fertile. Color 2.5Y 8/10.

*Pistil.*—Normally 1. Average length 16.6 mm. Surface — glabrous. Average height compared to stamen — approximately 1.7 mm lower. Color 2.5Y 9/2.

*Fragrance.*—Very slight.

*Blooming period.*—Date of First Bloom Mar. 2, 2003. Date of Petal Fall Mar. 11, 2003. Varies slightly with climatic conditions.

*Color.*— 2.5RP 8/6.

*Number flowers per flower bud.*—One.

*Pedicel.*—Average length 4.3 mm. Average width 2.7 mm. Color 2.5GY 8/6.

Fruit:

*Maturity when described.*—Firm ripe.

*Date of first picking.*—Aug. 13, 2003.

*Date of last picking.*—Aug. 18, 2003, varies slightly with climatic conditions.

*Size.*—Large. Average diameter axially 70.5 mm. Average transversely in suture plane 69.2 mm. Average weight 195 grams, average weight varies slightly with fertility of the soil, amount of thinning and climatic conditions.

*Form.*—Globose.

*Suture.*—Nearly smooth, extends from base to apex.

*Ventral surface.*—Nearly rounded, very slightly lipped.

*Apex.*—Usually rounded, varies from rounded to slight pistil point.

*Base.*—Flat to slightly retuse.

*Cavity.*—Rounded to slightly elongated in suture plane. Average depth 7.9 mm. Average diameter 11.9 mm.

Stem:

*Size.*—Medium. Average length 7.1 mm. Average diameter 3.2 mm.

*Color.*—Varies from 5GY 7/8 to 5GY 6/8.

Flesh:

*Ripens.*—Evenly.

*Texture.*—Firm, meaty.

*Fibers.*—Few, very small, tender.

*Firmness.*—Firm, holds firm on the tree 10 to 12 days after maturity, shipping ripe.

*Aroma.*—Moderate.

*Amydgalin.*—Undetected.

*Eating quality.*—Very good.

*Flavor.*—Very good, with a mild, sweet, low-acid flavor.

*Juice.*—Moderate amount, enhances flavor.

*Brix.*—Average 15.6°, varies slightly with amount of fruit per tree and climatic conditions.

*Color.*—Varies from 10YR 8/10 to 10YR 8/14. Pit cavity varies from 7.5R 4/10 to 7.5R 3/10, slight bleeding into flesh around pit cavity.

Skin:

*Thickness.*—Medium.

*Surface.*—Smooth.

*Pubescence.*—Wanting.

*Tendency to crack.*—None.

*Color.*—Ground color varies form 10YR 8/8 to 10YR 8/12. Nearly overspread with 7.5R 4/12 to 10R 4/12. Random areas of ground color partially exposed creating a mottling pattern to skin surface, primarily around apex area.

*Tenacity.*—Tenacious to flesh.

*Astringency.*—Undetected.

Stone:

*Type.*—Clingstone.

*Size.*—Large. Average length 34.2 mm. Average width 27.3 mm. Average thickness 19.0 mm.

*Form.*—Obovoid.

*Base.*—Usually straight, varies from straight to slightly rounded.

*Apex.*—Nearly rounded; very slight point, 1 mm length.

*Surface.*—Irregularly furrowed toward the apex, pitted toward base. Pits vary from round to elongated. Usually one furrow on each side of suture.

*Sides.*—Vary from equal to unequal, with one side extending further from suture plane.

*Ridges.*—Relatively wide with smooth surface.

*Tendency to split.*—Very slight.

*Color.*—Varies from 7.5YR 5/6 to 7.5YR 5/10 when dry.

Kernal:

*Form.*—Ovoid.

*Taste.*—Bitter.

*Viability.*—Viable, complete embryo.

*Size.*—Average length 17.5 mm. Average width 12.8 mm. Average thickness 6.8 mm.

*Skin color.*—Varies from 2.5Y 7/12 to 5Y 7/12 when dry.

Use: Dessert. Market — local and long distance.

Keeping quality: Good, held firm in cold storage 3 weeks at 38 to 42° F. with minimal loss of flavor, firmness or internal browning of flesh.

Shipping quality: Good, minimal bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth and being a productive and regular bearer of large size, firm, yellow flesh, clingstone fruit with very good flavor and eating quality; the fruit is further characterized by its high degree of attractive red skin color, holding firm on the tree 10 to 12 days after maturity and having good storage and shipping quality.

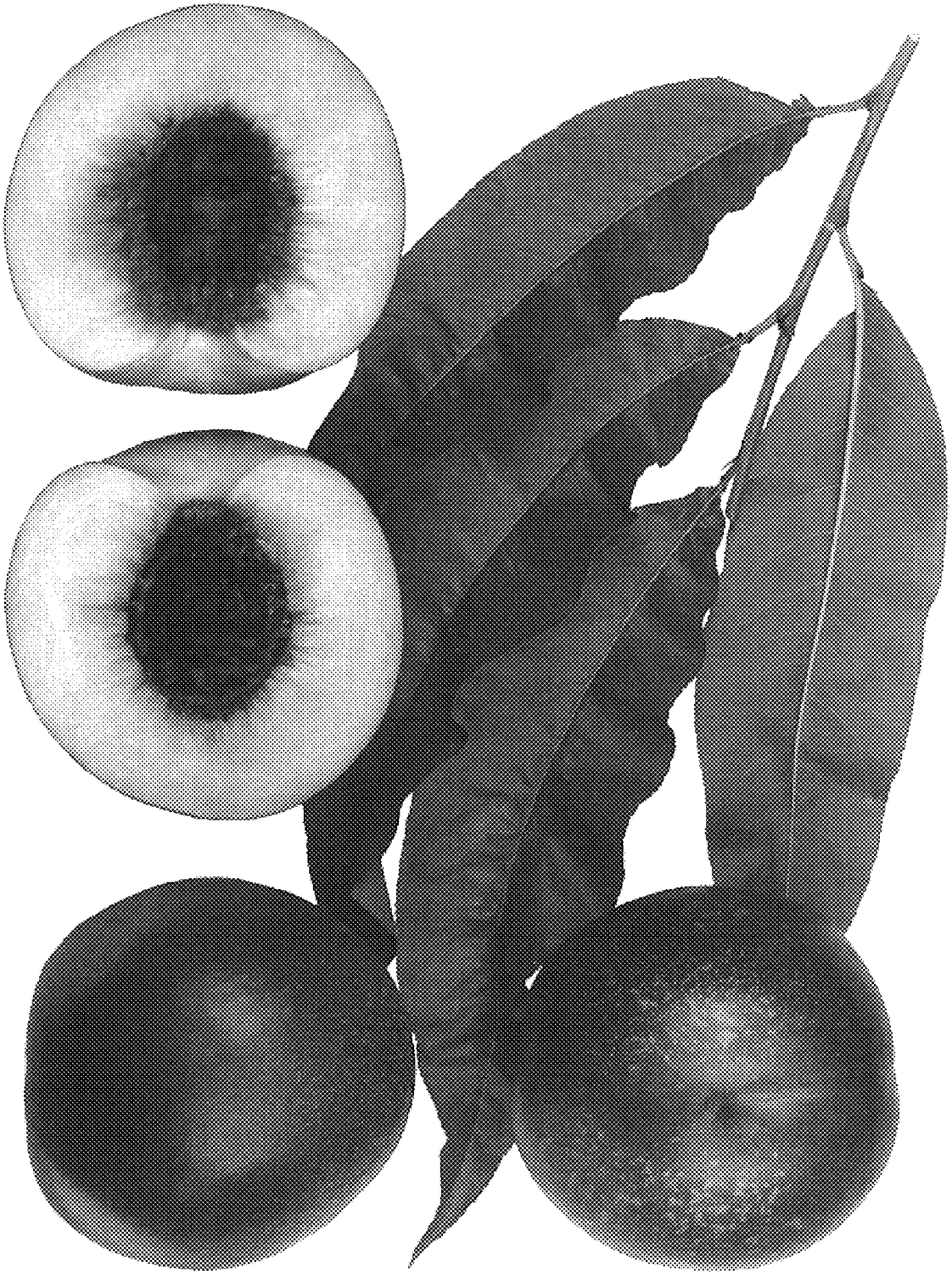

* * * * *